(12) United States Patent
Liniger et al.

(10) Patent No.: US 8,979,800 B2
(45) Date of Patent: *Mar. 17, 2015

(54) INSERTION DEVICE FOR INFUSION SETS

(75) Inventors: Jürg Liniger, Ostermundigen (CH); Mark Roethlisberger, Hasle-Rueegsau (CH); Simon Scheurer, Bern (CH)

(73) Assignee: Roche Diagnostics International AG, Rotkreuz (CH)

( * ) Notice: Subject to any disclaimer, the term of this patent is extended or adjusted under 35 U.S.C. 154(b) by 1400 days.

This patent is subject to a terminal disclaimer.

(21) Appl. No.: 11/427,437

(22) Filed: Jun. 29, 2006

(65) Prior Publication Data

US 2007/0016129 A1    Jan. 18, 2007

Related U.S. Application Data

(63) Continuation of application No. PCT/EP2004/010575, filed on Sep. 21, 2004.

(30) Foreign Application Priority Data

Dec. 30, 2003   (DE) .............. 203 20 207 U

(51) Int. Cl.
*A61M 5/20*       (2006.01)
*A61M 5/158*      (2006.01)

(52) U.S. Cl.
CPC ....... *A61M 5/158* (2013.01); *A61M 2005/1581* (2013.01); *A61M 2005/1585* (2013.01)
USPC ........................................ 604/157; 604/156

(58) Field of Classification Search
CPC .......... A61M 5/158; A61M 2005/206; A61M 2005/1585; A61M 5/3287; A61M 2005/1587
USPC ............ 604/134, 135, 136, 164.01, 137, 157, 604/164.07, 164.08, 164.12, 156, 158
See application file for complete search history.

(56) References Cited

U.S. PATENT DOCUMENTS

| | | |
|---|---|---|
| 4,085,748 A | 4/1978 | Boyer |
| 5,938,413 A | 8/1999 | Makino et al. |
| 6,293,925 B1 | 9/2001 | Safabash et al. |
| 6,302,866 B1 | 10/2001 | Marggi |
| 2002/0055711 A1* | 5/2002 | Lavi et al. ............ 604/110 |
| 2002/0091357 A1* | 7/2002 | Trautman et al. ........ 604/117 |
| 2003/0060781 A1* | 3/2003 | Mogensen et al. ........ 604/257 |
| 2005/0101912 A1* | 5/2005 | Faust et al. ............ 604/117 |
| 2007/0016129 A1 | 1/2007 | Liniger et al. |
| 2008/0009805 A1* | 1/2008 | Ethelfeld ............ 604/180 |

FOREIGN PATENT DOCUMENTS

| | | |
|---|---|---|
| DE | 2357745 | 5/1975 |
| GB | 1441599 | 6/1973 |

\* cited by examiner

*Primary Examiner* — Aarti B Berdichevsky
*Assistant Examiner* — Laura Schell
(74) *Attorney, Agent, or Firm* — Dinsmore & Shohl LLP

(57) ABSTRACT

An insertion device for infusion sets, comprising a housing for enclosing an infusion set, a drive device for displacing the infusion set for insertion, wherein a portion of the drive device moves in an insertion direction, the movement being substantially friction-free relative to the housing.

16 Claims, 16 Drawing Sheets

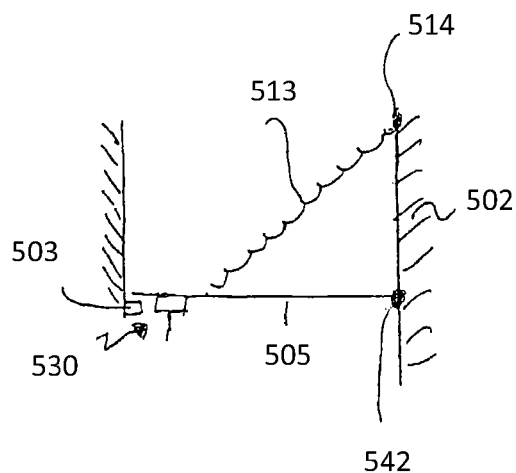 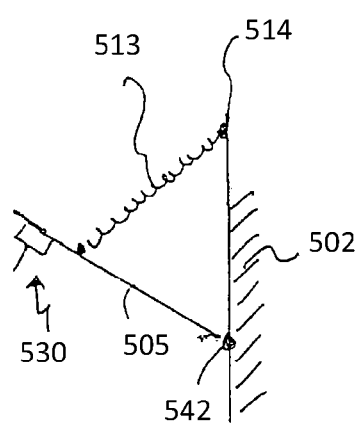
FIG. 12a
FIG. 12 b

INSERTION DEVICE FOR INFUSION SETS

CROSS-REFERENCE TO RELATED APPLICATION(S)

This application is a continuation of International Patent Application No. PCT/EP2004/010575, filed on Sep. 21, 2004, which claims priority to German Application No. 203 20 207.4, filed on Dec. 30, 2003, both of which are incorporated herein by reference.

BACKGROUND

The present invention relates to devices for delivering, administering, injecting or dispensing substances and to devices for extracting, measuring or sensing, and to methods of making and using both such devices. More particularly, it relates to an insertion device for piercing devices, for example, needles, infusion sets, needles for diagnostic purposes, sensor needles, e.g., for glucose measurement, and the like.

Infusion sets are known from U.S. Pat. No. 6,302,866, for example. Insertion devices for inserting infusion sets are known from U.S. Pat. No. 6,293,925, for example. Insertion devices of this type typically have a plunger which slides along the inner circumferential surface of the housing and which has a receiving device for receiving the infusion set.

SUMMARY

An object of the present invention is to provide an insertion device which allows the energy for introducing a piercing device, in particular an infusion set, to be transmitted, as far as possible without loss, e.g., with minimal friction, to the infusion set.

In one embodiment, the present invention comprises an insertion device for infusion sets, the insertion device comprising a housing for enclosing an infusion set and a drive device for displacing the infusion set for insertion, wherein a portion of the drive device moves in an insertion direction, the movement being substantially friction-free relative to the housing.

In one embodiment, an insertion device according to the present invention may be used for medical purposes, in particular for introducing piercing devices, e.g. infusion sets, into the skin without the patient having to insert the infusion set into the skin by his own force. This puncturing procedure is taken over for him by the insertion device. The term "piercing device" encompasses devices comprising needles, lancets, cannulas with one or more lumens as well as tubes with one or more lumens, e.g., tubes with one end designed to pierce skin, as well as insertion sets, sensors and sensor sets comprising at least one piercing member. The insertion device is a device designed for piercing skin, in particular human skin, which can comprise further means which are adapted for medical purposes, e.g., to deliver substances through the pierced skin, to extract substances through skin from the body, or to perform measurements in the body, in particular for diagnostic purposes. Below, the term "infusion set" is used as exemplary for and/or representative of a piercing device. The insertion device has a housing which is designed such that it surrounds a needle, contained in the infusion set, when the infusion set is placed in the insertion device. Moreover, the insertion device has a drive device for moving the infusion set, for accelerating it, in a predetermined direction, which may be referred to as the drive and/or insertion direction. The predetermined direction can be 90° to the skin or to the contact surface of the lower part of the housing. However, it can also be designed for an inclined direction of insertion, that is to say with a angle between 0 and 90°.

The insertion device according to the present invention is designed in such a way that the drive device has a structure allowing said drive device, and also the infusion set, to move relative to the housing in a manner free from sliding, and substantially free from friction relative to the housing. Therefore, the movable parts of the drive device are designed such that they do not slide in the drive direction but instead are free from sliding and/or free from contact and/or free from friction during a movement in the drive direction. More particularly, parts or components of the drive device moving in the drive or insertion direction are designed such that they are spaced apart from the housing.

In some embodiments, this is achieved by the fact that the drive device bears on the end of the housing (hereinafter also called the "upper end") which lies remote from the outlet end of the infusion set (hereinafter also called the "lower end"), and, by virtue of the construction or nature of the drive device, a movement in the direction toward the side walls of the housing, which extend along the drive device, is avoided or reduced, in order to avoid a contact between the housing and the parts of the drive device moving in the drive direction.

In some embodiments, the drive device has a drive mechanism connected to the housing. The connection is made at the end of the housing remote from the outlet end of the infusion set (in other words at the upper end). However, as will be explained below, it can also be present on a side wall of the housing. In the text below, the lower end of the infusion device indicates that end from which the infusion set emerges in order to pierce the skin. The upper end is the end remote from this one. The upper end and lower end are connected by side walls of the housing.

In some embodiments, to propel the drive device and the drive mechanism, a tensioning means is used which, through the action of an external force, can store energy, for example an elastic means which is compressed. Any other suitable mechanical, electrical or chemical drive means can be used.

In one embodiment, an insertion device according to the present invention has a drive endpiece (e.g. hammer head) which is designed to move an infusion set in a drive direction. The drive endpiece is therefore in contact with the infusion set, at least temporarily, to accelerate it.

The drive endpiece can advantageously be pretensioned relative to the housing, e.g., to the upper end of the housing and/or to a side wall of the housing, by a tensioning means, such as an elastic means, and/or with the aid of a drive mechanism. In one preferred embodiment, in an insertion device according to the invention the drive endpiece is moved in the drive direction upon release of the energy stored in the drive means, upon release of the pretensioning. The drive endpiece transmits its impulse to the infusion set, which is arranged at the lower end of the drive endpiece or is mounted in such a way that it lies in the path of movement of the drive endpiece so as to take up the impulse of the drive endpiece.

In some embodiments, the drive device can be locked in the pretensioned state, and the lock can be undone by actuation of a release member (for example a switch or press button).

In some embodiments, the drive device advantageously comprises a lever mechanism. This is used to move the drive endpiece relative to the housing, and in the drive direction. The rigid members of the lever mechanism which turn about pivot points are referred to hereinbelow as leg levers, while the pivot points are referred to as rotary connection members. The leg levers of the lever mechanism are at least partially pretensioned relative to the housing so as to then execute a movement predetermined by the arrangement of the leg levers and rotary connection members such that the drive endpiece is moved in the drive direction. The lever mechanism is advantageously configured such that the parts of the lever mechanism which move in the drive direction are spaced apart from the housing or, at least, do not execute any sliding movement relative to the housing. To achieve this while at the same time ensuring a stable guiding of the drive endpiece in a predetermined direction, in some preferred embodiments, the lever mechanism has at least two arms which each have one, two or more leg levers, the two or more leg levers of one arm being connected via rotary connection members. These two arms are mechanically coupled such that a stabilization of the drive movement is afforded by the fact that a movement transverse to the drive direction is counteracted by the coupling. The coupling (e.g. by gears or toothed wheels) is configured such that the two arms are moved synchronously in the drive direction.

In some embodiments, the lever mechanism is configured such that the rotary connection members, via which the leg levers are pivotably connected, are at least in part movable in the drive direction, that is to say are also spaced apart from the housing during a movement in the drive direction.

In a design with two arms, the lever mechanism has two first rotary connection members which turn in opposite directions during movement in the drive direction and which can be moved in the drive direction. Two second rotary connection members are also provided, but they are positionally fixed and are connected to the housing. These two second rotary connection members are coupled in their rotary movement, for example by a gear, a transmission member with teeth, or the like. Their rotary movement too is counter-directional. A first and a second rotary connection member are situated in one arm of the lever mechanism, and there is the same setup in the other arm too. In each arm, the first and second rotary connection members are connected via at least one leg lever.

The present invention comprises, among others, the following embodiments A to G, the displacement mechanism representing one example of the drive device, and the bearing axles representing one example of the rotary connection members:

A. An insertion device for subcutaneously inserting a cannula of an infusion set which is held releasably in a receiving element of a displacement mechanism, wherein the displacement mechanism has leg levers mounted rotatably in the housing of the insertion device.
B. An insertion device according to embodiment A, wherein the interaction of several leg levers ensures an axial displacement of the receiving element.
C. An insertion device according to embodiment B, wherein four leg levers interact.
D. An insertion device according to embodiment C, wherein two upper leg levers are mounted rotatably in the housing of the insertion device via bearing axles at their end.
E. An insertion device according to embodiment D, wherein the two upper leg levers have teeth meshing with one another at their bearing ends.
F. An insertion device according to embodiment E, wherein two lower leg levers are in toothed engagement at bearing ends connected to the receiving element.
G. An insertion device according to embodiment F, wherein the leg levers are connected to one another via connection axles.

The insertion device can also be designed without a lever mechanism, for example with an elastic means which is fitted on the housing at the upper end of the insertion device, while the drive endpiece is provided at the lower end of the elastic means. By compression of the elastic means, energy is stored which is then released, via a release mechanism, to move an infusion set in the drive or insertion direction by expansion of the elastic means. The infusion set in turn can either be fitted on the drive endpiece itself or can be located on the housing and in the path of movement of the drive endpiece. By the contact between drive endpiece and infusion set, the latter is then struck out of a holding fixture on the housing and accelerated downward to the outlet end. In some preferred embodiments, the elastic means is provided with an inherent stiffness in the direction perpendicular to the drive direction, to prevent the elastic means from coming into contact with the housing and thus losing drive energy. The housing is designed in such a way that, even in the event of a certain lateral movement of the drive endpiece and of the elastic means, both do not come into contact with the housing. The lateral movement is less than approximately 20%-10% of the full stroke of the elastic means from compressed position to released position.

In some embodiments, the elastic means can, for example, be a steel spring or a foam. The foam can be in a cuboid shape, for example. Longitudinal channels can be provided in the foam in the drive direction, through which extensions pointing down from the upper end of the housing can engage in order to provide the elastic means with lateral guidance and thus prevent a (excessive) sideward movement. A tensioning rod can also be guided through the elastic means thereby to fulfill two functions. The first function is the guiding of the elastic means, and the second function is the compression of the elastic means by drawing the tensioning rod up from the housing. For this purpose, a suitable aperture is provided in the upper end of the housing, and the tensioning rod extending through the elastic means is secured at the lower end of the elastic means, for example on the drive endpiece. It is also possible to provide lateral charging grips which can be moved upward through lateral longitudinal slits in the housing in order to move the drive endpiece upward to compress the elastic means. A locking member is provided on the housing, into which locking member it is possible, for example, to engage the charging grips, the drive endpiece or a charging bar which, for this purpose, have a depression or extension that can be brought into engagement with the locking member.

The aforementioned compressible plastic, for example foam, can also be combined with another elastic means, for example a metal elastic means such as a spring. The elastic means, for example based on plastic, for example a foam, or an elastomer, then serves as a guide, while the metal elastic means, e.g., the spring, serves as additional energy source. For example, the elastic means could be designed as a hollow cylinder or hollow cube and the spring could be arranged lying on the inside. This arrangement can of course also be reversed, so that the physically constituted elastic means is provided, e.g. as a solid body, in the inner axis of a helical spring and is surrounded by the spring.

Since the elastic means serves at the same time as a guide, the insertion device can be made very small, and the distance between the upper end and lower end of the housing can be made small, and there is very little noise development upon use of the insertion device.

According to a further preferred embodiment, a drive endpiece is articulated via levers on the side of the housing. In this case, the drive endpiece is elongate in the drive or insertion direction, to permit the drive endpiece to be connected to the side wall of the housing at two or more locations via levers. On the drive endpiece, there is at least one rotary connection member which is connected to at least one leg lever. In some preferred embodiments, at least two leg levers are provided between the rotary connection member on the drive endpiece and a rotary connection member on the wall of the housing. The two leg levers have different lengths. The lengths are such as to permit, as far as possible, a rectilinear movement of the drive endpiece in the drive direction. This is achieved by the fact that, between the two leg levers connecting the rotary connection member to the wall of the housing, a further rotary connection member is provided which is connected to the drive endpiece and to the wall of the housing only via the leg levers. The connection of the drive endpiece to the wall of the housing is in the form of a lemniscate guide. The infusion set is arranged or can be fitted at the lower end of the drive endpiece, or it is struck from a holding fixture on the housing by the lower end of the drive endpiece.

To tension the drive endpiece, the latter can be connected, for example, to the upper end of the housing via an elastic means. Alternatively or in addition to this, the levers can be designed such that they can be pretensioned against an upper or lateral wall of the housing by elastic means, to thereby accelerate the drive endpiece downward when the tension of the elastic means is released. In addition, it is also possible once again to provide a release mechanism, a tensioner, and a locking mechanism for locking the tensioned state.

In a further embodiment according to the invention, the drive endpiece is designed as a leg lever, one end of the leg lever being connected to the wall of the housing, e.g., a side wall, via a rotary connection member. The other end is used to strike an infusion set out of a holding fixture or to receive this infusion set. An elastic means tensions the leg lever against the wall of the housing such that said leg lever is forced away from the wall of the housing when the tension is released. The leg lever pivots about the rotary connection member in such a way that the free end strikes the infusion set out of the holding fixture when the leg lever has been tensioned, perpendicular to the application direction of the infusion set, by the elastic means. If the infusion set is fitted at the free end, the infusion set emerges from the housing for application of the needle when the leg lever is perpendicular to the application direction. The infusion set is thus arranged in such a way that the needle is at least approximately perpendicular to the direction of extent of the leg lever and points downward in the nontensioned state, whereas, in the tensioned state, the needle points obliquely downward, that is to say is at an angle with respect to the application direction.

According to a further embodiment of the invention, an expandable elastic means is provided, e.g., an elastomer part. This is arranged in the housing in such a way that it is expanded when the drive endpiece is moved counter to the application direction. For this purpose, the elastomer part is anchored, mounted or guided under the drive endpiece and is additionally connected to the drive endpiece. Since the holding, guiding or anchoring lies deeper than the drive endpiece, the elastomer part is tensioned when the drive endpiece is moved upward, until it reaches a locked position. This locked position is then released via a release mechanism such that the drive endpiece is accelerated downward by means of the expanded elastomer part which contracts again. The infusion set can once again be arranged on the drive endpiece or can be struck from a holding fixture by the drive endpiece. To achieve a downward movement which is as rectilinear as possible and parallel to the inside walls of the housing, the elastomer part is arranged symmetrically about the drive endpiece and can be divided into several bands, for example, which are arranged symmetrically with respect to the path of movement of the drive endpiece. As in the other embodiments too, the path of movement runs or extends parallel to the inside wall of the housing. In some embodiments, a rigid sleeve can be provided about whose lower end the elastomer part is guided, in which case the lower end of the sleeve and thus of the guided elastomer part at least approximately coincides with the plane of emergence from which the infusion needle emerges from the insertion device upon application. The lower end of the elastomer part is deeper than the drive endpiece when the latter is located at the upper end of its path of movement.

In any embodiment of the present invention, the infusion set can be brought into contact with the drive endpiece in different ways so as to apply the infusion set. For example, the infusion set can be secured on the drive endpiece by means of a form fit, a force fit and/or frictional engagement. The drive endpiece can enclose the infusion set, or the infusion set can be plugged onto the drive endpiece. In this case, the infusion set has, for example, an extension which engages in a corresponding recess of the drive endpiece or, conversely, the drive endpiece has an extension which engages in a depression of the infusion set. Alternatively, the infusion set can also be mounted on the housing such that it projects into the path of movement of the drive endpiece. The drive endpiece then strikes the infusion set out of the holding fixture during its movement from the top downward, and the infusion set flies freely onto the skin in order to apply or insert the needle.

BRIEF DESCRIPTION OF THE DRAWINGS

FIGS. 8a, 8b and 8c, shows a variant of the device of FIG. 3.

FIGS. 9a and 9b, show the device of FIG. 8 in a released state.

FIG. 10, including

FIG. 12, including FIGS. 12a and 12b, shows another embodiment of the present invention.

FIG. 13, including

FIG. 14, including

FIG. 15, including

DETAILED DESCRIPTION

In the description below, identical reference numbers designate identical parts, unless otherwise stated. Features, functions and/or structures of different embodiments can be combined with one another.

Figure 1:
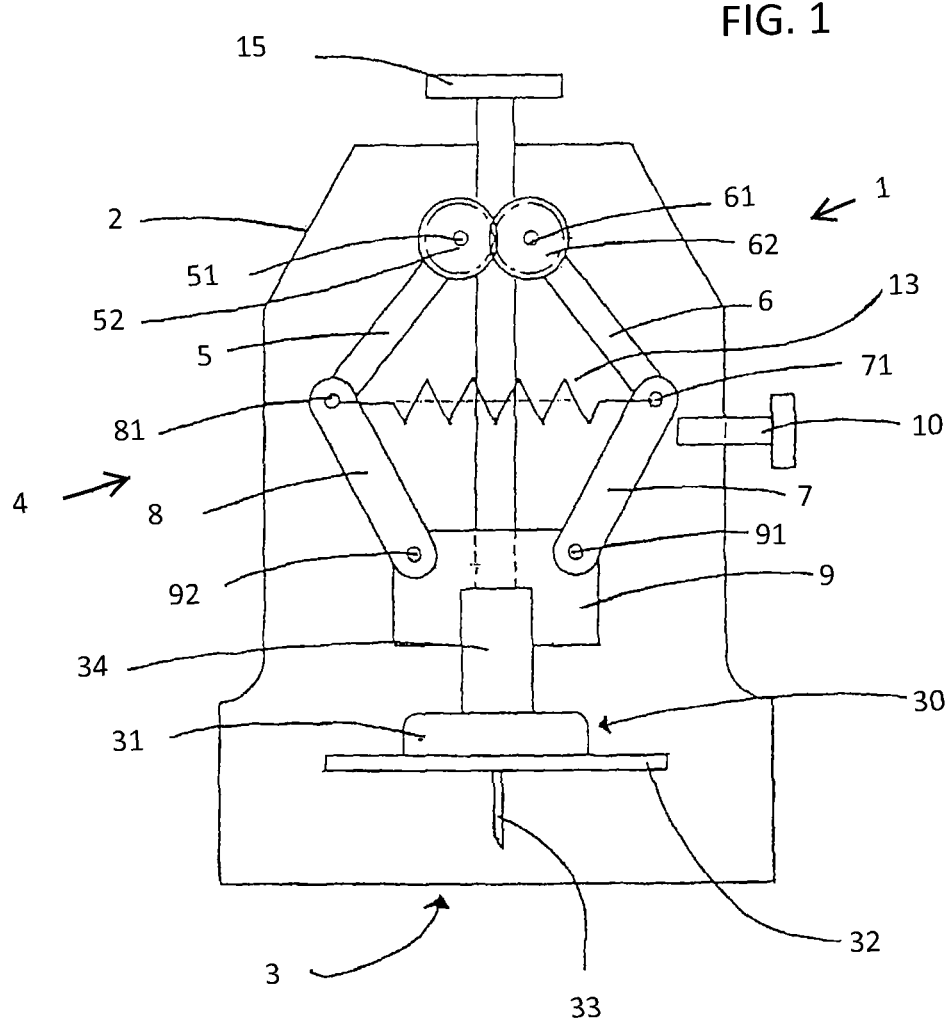
FIG. 1 is a schematic representation of one embodiment of an insertion device according to the present invention.

FIG. 1 shows a schematic representation of an insertion device 1, with a housing 2, with a housing aperture 3 on the underside, with an infusion set 30 which is held releasably and in an axially displaceable manner in the housing 2, and with a corresponding displacement mechanism 4.

The displacement mechanism 4 has four interconnected leg levers 5, 6, 7, 8. The two upper leg levers 5, 6 are mounted rotatably in the housing 2 at their bearing ends 52, 62 by way of their own bearing axles 51, 61. In addition, the bearing ends 52, 62 mesh with one another via teeth (FIG. 2), comparable to a compass as described in DE 2,357,745. Both upper leg levers 5, 6 are connected via connection axles 71, 81 to the lower leg levers 7, 8, which in turn are mounted by way of bearing axles 91, 92 on a receiving element 9 for the infusion set 30. By means of this connection of the individual leg levers 5, 6, 7, 8 to one another and to the housing 2 or receiving element 9, a pivoting of the upper leg levers 5, 6 with respect to one another results in an axial displacement of the receiving element 9 and, consequently, of the infusion set 30 toward the housing aperture 3. Upon maximum pivoting of the leg levers 5, 6 with respect to one another, the underside 32 of the infusion set lies slightly outside the housing aperture 3. The displacement mechanism also has an elastic element or member 13, for example a spring, which in FIG. 1 is arranged between the upper leg levers 5, 6 and causes a pivoting movement of the upper leg levers 5, 6 with respect to one another. It would be likewise possible to arrange the spring 13 between housing 2 and at least one leg lever 5, 6, above the connection axles 71 and 81 between the upper and lower leg levers.

By way of a release device, for example, a release button 10, the displacement mechanism is freed from a tensioned to a non-tensioned position.

An infusion set 30 usually comprises a head 31, a holding element 34 arranged thereon, an adhesive underside 32, and a cannula 33 for penetrating the skin. Depending on the design of the cannula 33, either from easily bendable material, for example Teflon, or harder material, for example steel, the cannula 33 can itself penetrate the skin or may require an additional insertion cannula (not indicated). Fitted on the catheter head is an infusion catheter (not shown) which creates a fluidic connection between the cannula 33 and an administration device (not shown), for example an insulin pump.

In use, an infusion set 30 is arranged on the receiving element 9 by means of a holding element 34, and, by moving the receiving element 9 away from the housing aperture 3, the displacement mechanism 4 is brought from the non-tensioned to the tensioned position. The housing 2 of the insertion device 1 is pressed with the housing aperture 3 onto the skin. By actuating the release button 10, a movement of the upper leg levers 5, 6 with respect to one another and, consequently, a movement of the receiving element 9 and of the infusion set 30 in the direction of the housing aperture 3 is instigated. The displacement mechanism 4 forces the cannula 33 under the skin and at the same time forces the adhesive underside 32 onto the surface of the skin. To allow the catheter head 31 to be removed from the insertion device 1 in a way which is as painless as possible, actuation of an ejector device 15 releases the holding element 34 from the receiving element 9. In the simplest case, the holding element 34 is held in the receiving element 9 by means of frictional engagement, such that the ejection takes place by means of light axial pressure being exerted on the holding element 34 via the ejector device 15, for example in the form of a drive rod.

Figure 2:
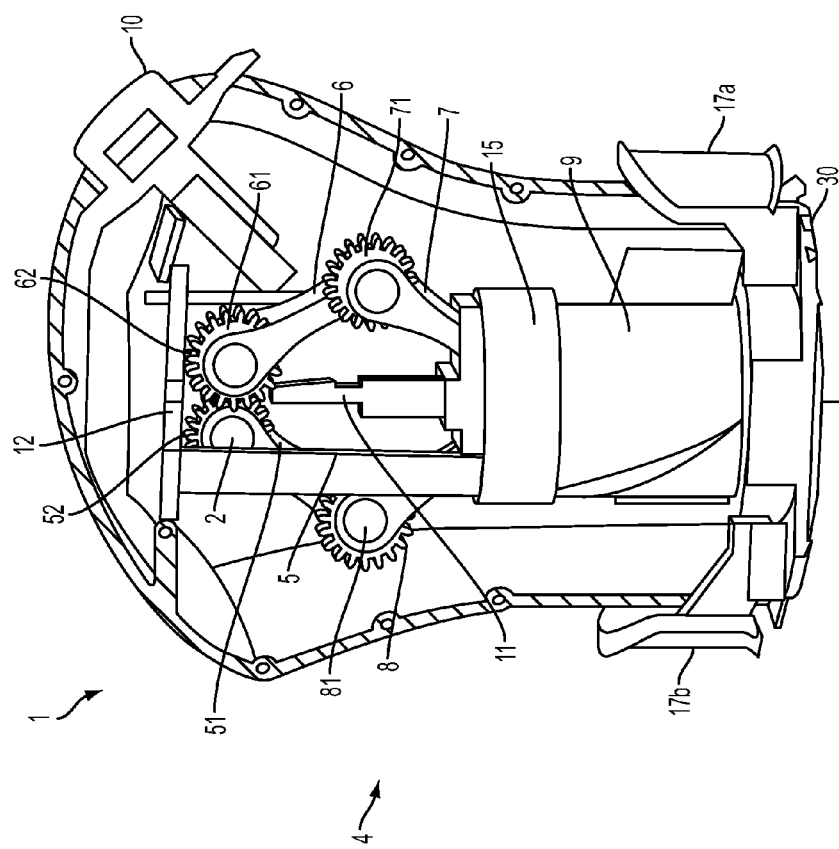
FIG. 2 is a modified embodiment of the insertion device of FIG. 1.

FIG. 2 shows a modified insertion device. Here, the displacement mechanism 4 also has four interconnected leg levers 5, 6, 7, 8, the two upper leg levers 5, 6 being mounted in the housing 2 by way of bearing axles 51, 61 at their bearing ends 52, 62, and meshing with one another via teeth. Both upper leg levers 5, 6 are connected by connection axles 71, 81 to the lower leg levers 7, 8, which in turn are mounted in a receiving element 9 for the infusion set 30 by way of bearing axles 91, 92. In this embodiment, the ends of the lower leg levers 7, 8 arranged around these bearing axles 91, 92 also mesh with one another via teeth (not shown) in order to ensure that the receiving element 9 cannot buckle to the side. Such buckling would have the effect that, during the insertion process, the cannula 33 would not move perpendicular to the surface of the skin.

Actuation of the release button 10 leads to a sideward movement of a locking lug 11, arranged on the receiving element 9, from a holding fixture 12 arranged in the housing 2 and, consequently, to the release of the displacement mechanism 4 from a tensioned to a non-tensioned state.

In use, movement of grip elements 17a, 17b in the direction of the release button 10 tensions the displacement mechanism 4 and engages the locking lug 11 in the holding fixture 12. Actuation of the release button 10 leads to a sideward movement of the locking lug 11 and, consequently, to release from the holding fixture 12 and thus to release of the displacement mechanism 4 from a tensioned to a non-tensioned position. When the cannula 33 is arranged under the skin, renewed actuation of the release button 10 causes a slight axial movement of the ejector device 15 and thus, via cams (not shown), an axial movement to the infusion set 30 held by frictional engagement in the receiving element 9. This movement suffices to eject the infusion set 30 from the receiving element 9.

Figure 3:
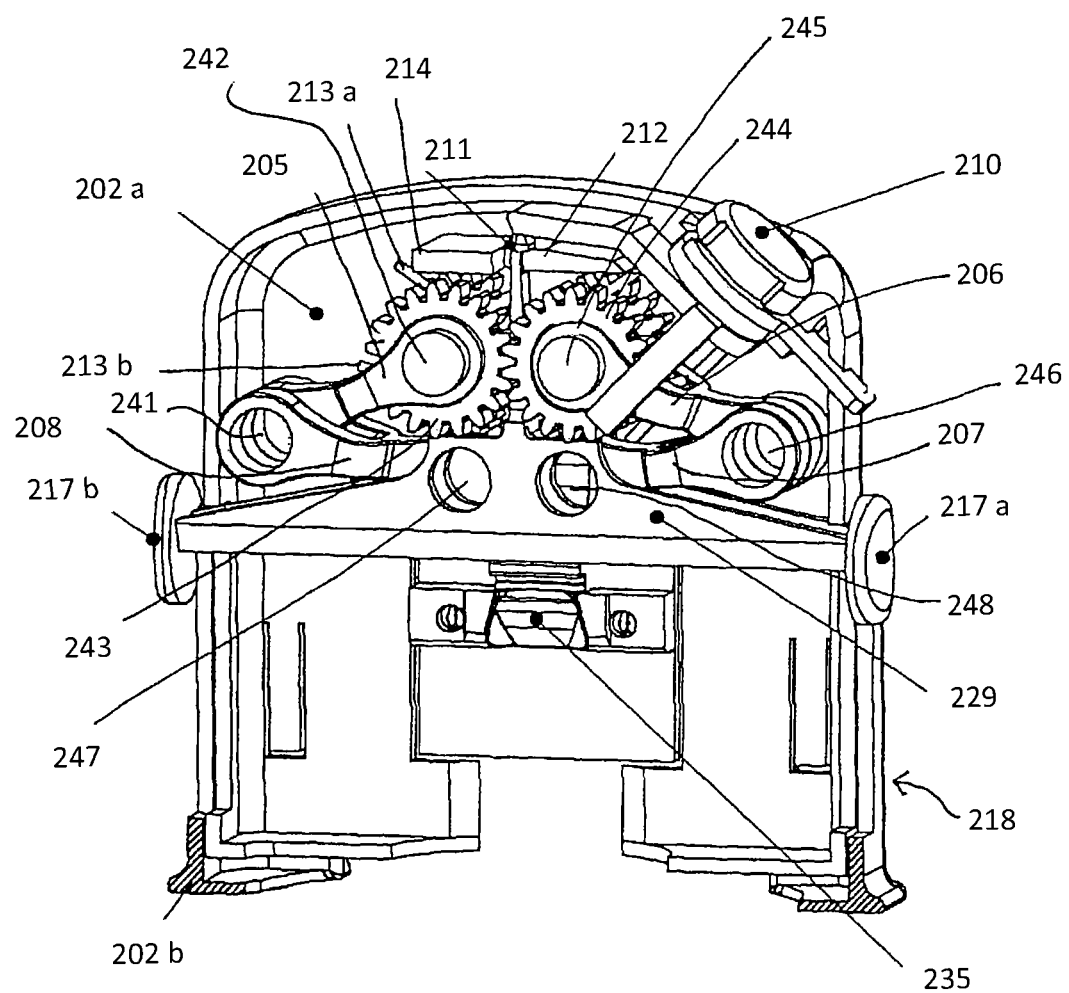
FIG. 3 shows a first position of another insertion device according to the present invention.

FIGS. 3 to 7 show a second exemplary insertion device according to the present invention which likewise is based on the principle of a lever mechanism. FIG. 3 shows the insertion device without infusion set in the tensioned state. FIG. 3 indicates a spring 213 which is visible at its ends 213a, 213b. One end 213a bears on an abutment 214 which is connected to the housing 202a in a positionally fixed manner. The other end of the leg spring 213 presses against the leg lever 205 and seeks to press this downward in FIG. 3. The spring is prevented from doing this by the latch 211 which, with a hook, is engaged on a rib 212 at the upper end of the housing. The rib 212 is connected to the housing 202 in a positionally fixed manner. The leg lever 205 is connected to another leg lever 208, arranged below it, via a rotary connection member (axle) 241 which ensures a rotation of the leg levers 205 and 208 about the common axle 241. A further rotary connection member 242 is arranged at the upper end of the leg lever 205. The rotation axle of the connection member 242 is positionally fixed, in contrast to the rotation axle 241. Arranged on the axle of the connection member 242 is a toothed wheel 243 which rotates together with the upper end of the leg lever 205. The toothed wheel 243 meshes with a toothed wheel 244 which rotates about a rotary connection member 245 or an axle 245. This toothed wheel 244 is connected to the upper end of the leg lever 206 in such a way that it co-rotates with the latter. Thus, a rotation movement of the leg lever 205 about the axle 242 causes, via the meshing toothed wheels, a corresponding rotation movement of the leg lever 206 in the opposite direction about the axle 245. A second leg spring is provided whose one leg is likewise supported on the housing, while the other one forces the leg lever 206 downward. A rotation movement about the axle 245 caused by this is likewise transmitted via the toothed wheels 244 and 243 to the leg lever 205.

The leg lever 205 is connected via the rotary connection member 241 to the leg lever 208, which in turn is connected via a rotary connection member 247 to a hammer head or plunger 244 which serves as a drive endpiece. Correspondingly, the leg lever 207 is connected to the hammer head 224 via a rotary connection member 248.

Grip elements 217a and 217b are connected fixedly to the hammer head 224. The hammer head 224 extends through elongate slits 218 located on both sides of the housing, and specifically in a manner free of contact, so as to have no friction losses. In the position shown in FIG. 3, the hammer head is at its uppermost end.

Figure 4:
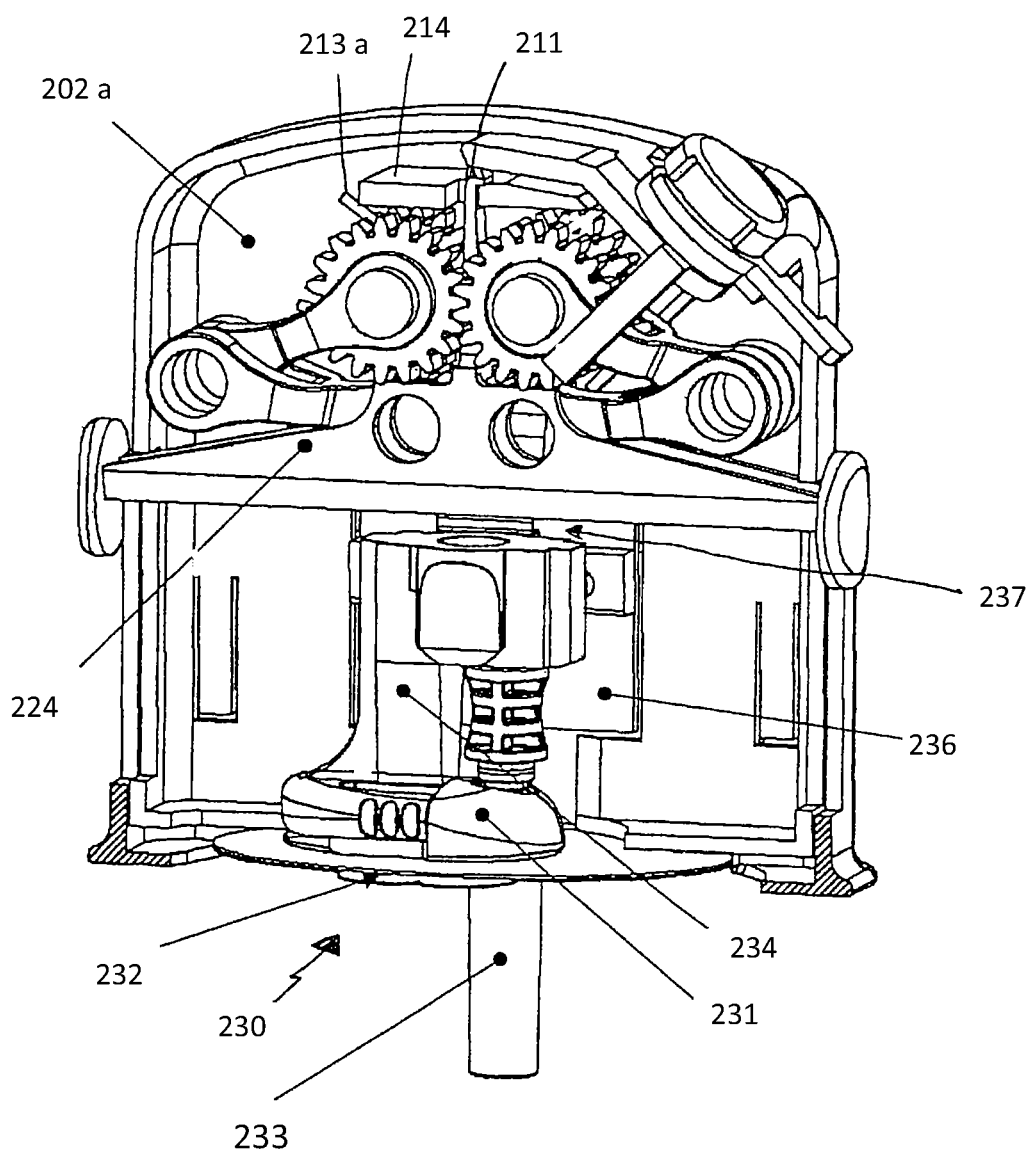
FIG. 4 shows a second position of the insertion device of FIG. 3.

A recess or receiving element 235 serves to receive an infusion set, as can be seen in FIG. 4. The housing is designed in two parts, namely with parts 202a and 202b, and the part 202b can be pushed downward, as will be discussed later in connection with FIG. 5.

As has already been mentioned, an infusion set 230 is shown which comprises the following components: head 231, main part 234, protective sleeve for the cannula 233, and what is called a liner or adhesive plaster 232. The infusion set 232 is fitted on the receiving element 235 which is now concealed in FIG. 4 and which is connected to the rear wall 236 of the housing. As can be seen from FIG. 4, a gap 237 is present between the infusion set 230 and the hammer head 234 when the latter is in the locked state, that is to say the locking lug or latch 211 is locked, as has already been discussed with reference to FIG. 3.

Figure 5:
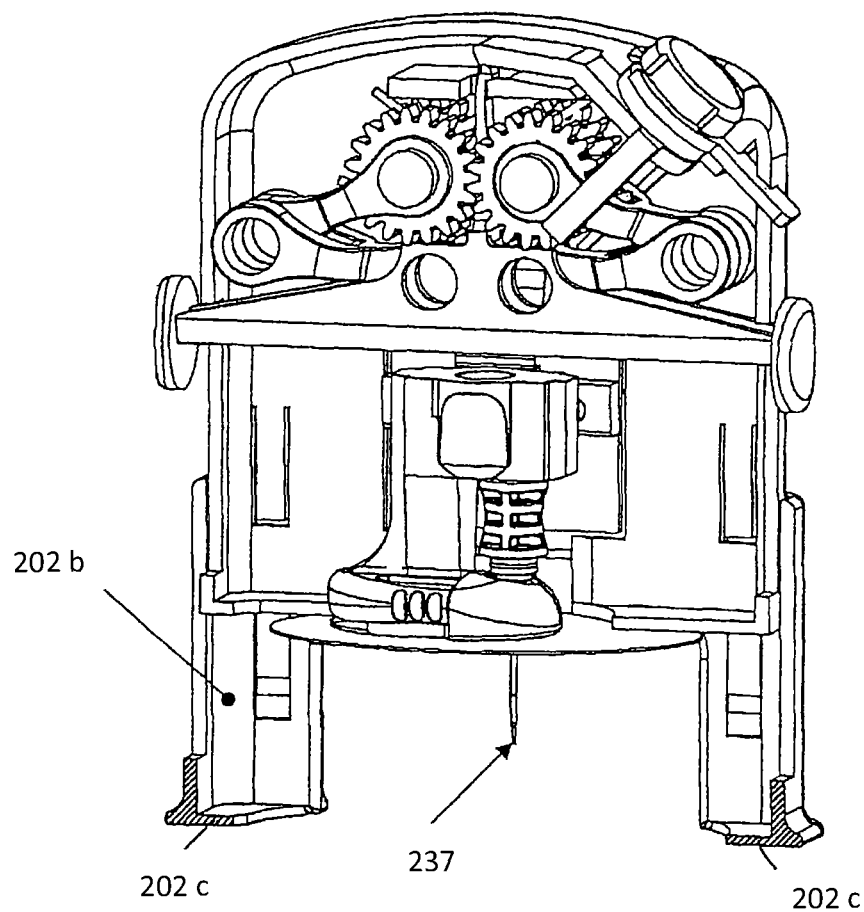
FIG. 5 shows a third position of the insertion device of FIG. 3.

FIG. 5 now shows the insertion device in a ready for use state. The insertion device is charged or loaded with the infusion set. The protective sleeve 233 has been removed, so that the cannula 237 now projects freely. The lower housing half 202b has been drawn out and thus surrounds and protects the exposed cannula 237. The lower ends 202c of the housing 202b may be generally flat to ensure a good placement of the housing on the skin.

Figure 6:
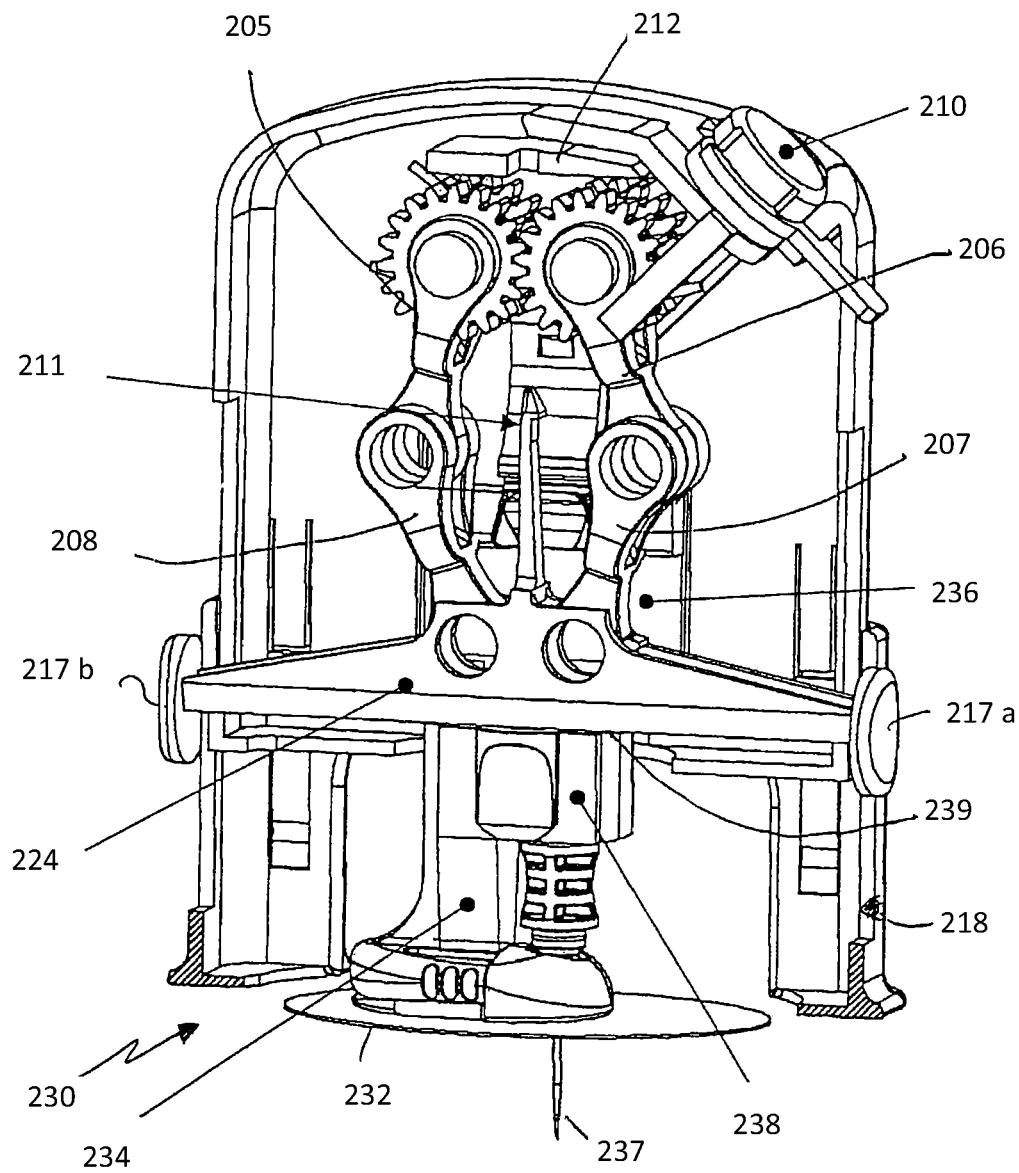
FIG. 6 shows a fourth position of the insertion device of FIG. 3.

FIG. 6 shows the insertion device after the release button 210 has been actuated and the cannula has penetrated into the skin. As will be seen, the liner 232 protrudes below the housing, as of course does the cannula or needle 237, such that the latter can penetrate into the skin unimpeded by the housing. The leg levers 205 and 206 have been forced downward by the relaxing of the leg spring 213 and by another leg spring (not shown) after the locking lug 211 has been released from the rib 212 by way of the release button 210. The leg levers 205, 206, 207 and 208 are now in the extended state and have turned about the respective connection members. By this means, the hammer head 224 has been driven down in its drive direction. By virtue of the sufficiently widely dimensioned gap 218, the hammer head has also been moved forward without friction and without contact in this gap, and the grip elements 217a and 217b are now located in their lower end state.

While the hammer head has been driven forward in the downward direction, it has struck against the upper end 239 of the infusion set 230 and thus released it from the receiving element 235 in which the infusion set has been held by form fit, force fit and/or friction. As a result of inertia, from this point onward, the infusion set 230 flies in the same direction as the hammer head 224 moves, and the cannula 237 thus pierces the skin. The infusion set thus moves in a free flight and unguided. However, optimal puncturing results were able to be achieved, since friction losses resulting from guidance of the infusion set have been avoided.

Figure 7:
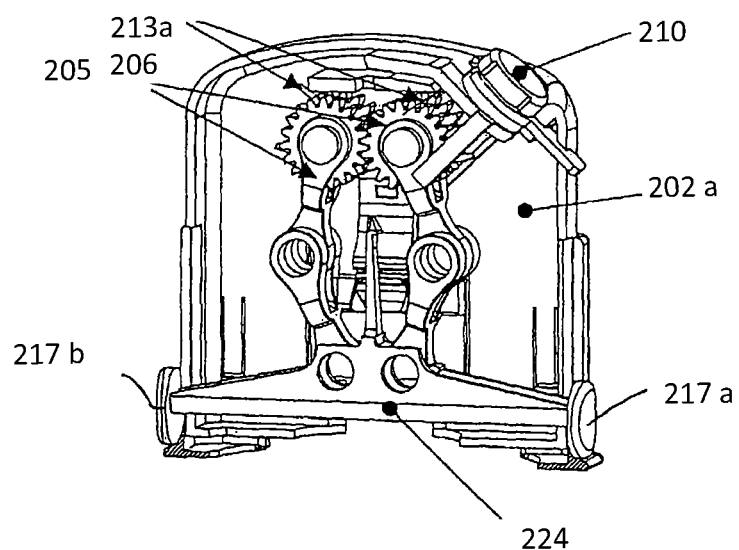
FIG. 7 shows a fifth position of the insertion device of FIG. 3.

FIG. 7 now shows the insertion device in a state before it is tensioned again and in a state in which no infusion set has yet been introduced. By pressing the grip elements 217a and 217b up toward the spring 213, the hammer head 224 is brought back up to its charged position.

The holding fixture for the infusion set on the housing can be configured in different ways. For example, the upper end of the infusion set can be held with force-fit between two receiving elements 235 serving as clamping fixtures. One clamping fixture 235 is mounted on one wall of the housing 202a, and the other lies opposite it. The distance between the clamping fixtures is greater than the width of the hammer head 224, so that the latter can pass without contact between two opposite clamping fixtures 235 and can carry the infusion set with it and release it from the clamping fixture.

As an alternative to clamping, the receiving element 235 can also be designed such that it has, for example, extensions which point downward, and the infusion set is then fitted from below onto these extensions, the infusion set having corresponding depressions so as to produce, for example by means of frictional engagement, the plug connection between infusion set and extension. The extension and the depression are once again arranged such that the hammer head, during its movement in the drive direction, can pass without making contact with it and then carries the infusion set with it.

Further to the above description, it will be noted that the leg springs may be mounted about the axles 242 and 245. For the case of frictional or form-fit engagement with the infusion set to be introduced, the receiving elements 235 are provided with elastic means which acts perpendicularly or transversely with respect to the drive direction, and in which two elastic means lying opposite one another clamp the infusion set securely, this also being able to be achieved, of course, with a single elastic means.

As will be seen from FIG. 8b, the receiving elements 235 press laterally against the infusion set so as to securely clamp it. The pressing action is effected by means of the elastic elements 251 which, for example, are helical springs. FIG. 8c shows a plan view of FIG. 8b. If the hammer head 224 now strikes against the upper end of the infusion set 230, the receiving elements 235 are forced back counter to the spring force of the springs 251, and the infusion set flies downward, freely accelerated by the force of the impacting hammer. FIG. 8b is a sectional view along the line A-A in FIG. 8a.

In one embodiment, the receiving elements 235 are thrust pins which, upon insertion of the infusion set, produce an audible click in order to show the patient that the infusion set has been correctly inserted. Abutments 252 and 253 are also arranged above the infusion set to obtain a correct position of the infusion set. The distance "d1" between hammer head and infusion set is in the range of approximately 0 to 10 mm.

Figure 8:
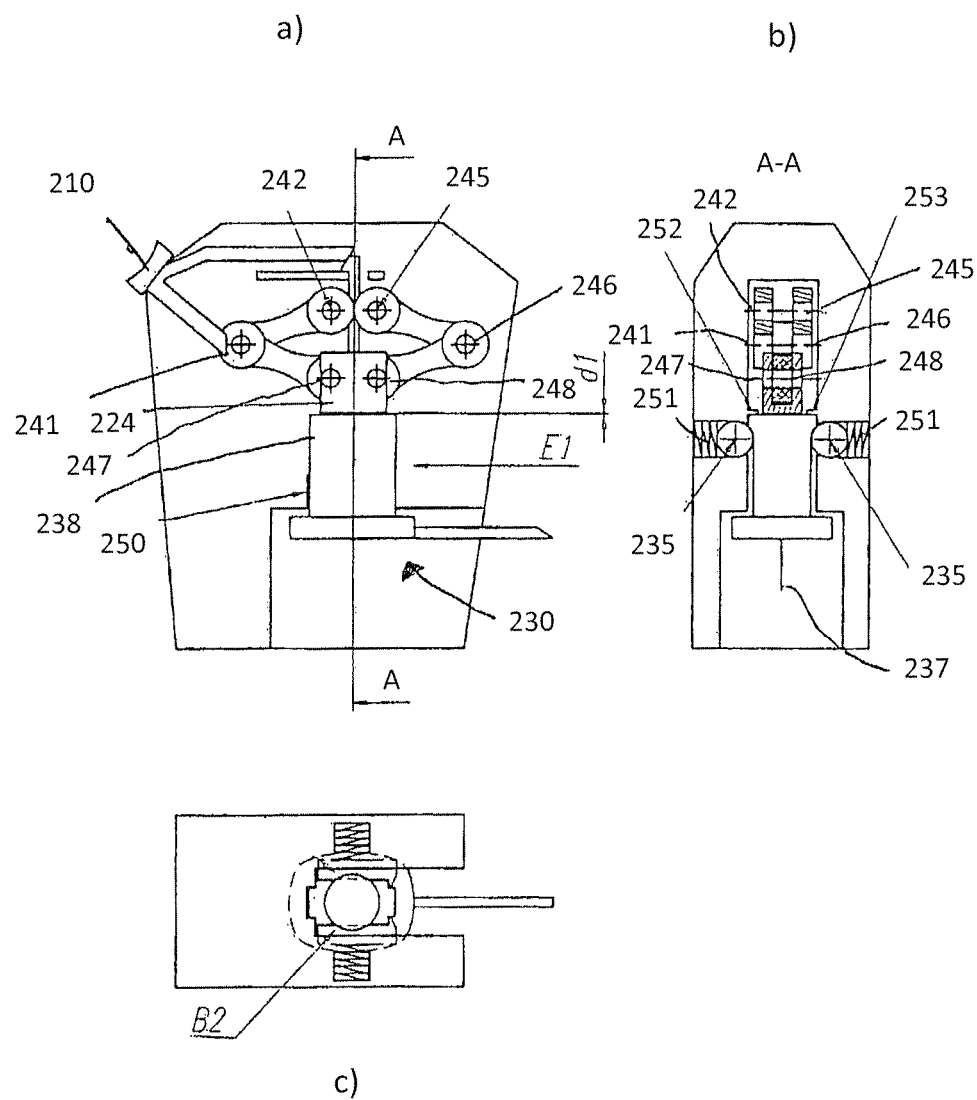
FIG. 8, including

The protective sleeve (needle guard) and the protective paper may be removed after the infusion set has been secured in its starting position, that is to say in the tensioned position shown in FIG. 8. By virtue of the secure clamping of the infusion set and locking by the locking lug 211, this can be done without danger. The insertion device is now ready to apply the infusion set. For this purpose, the infusion set is placed onto the skin at the intended site. To release it, all that has to be done is to actuate the button 210. By this means, the locking lug (snap-in hook) is deflected and the snap-fit connection thus released. The pretensioned mechanism is then accelerated downward, and the hammer head strikes against the infusion set after a free flight (without contact with the housing). The hammer head exerts on the infusion set a downward vertical force component which transmits laterally to the receiving elements 235 (thrust pins). By this means, the springs are compressed, leading to release of the infusion set. The infusion set is now applied into the body by the spring force of the pretensioned levers. The distance "d2" shown in FIG. 9a between hammer head and infusion set after release does not have to be defined. Depending on the curvature of the skin at the application site, the infusion set is in contact or not in contact with the hammer. After the puncturing procedure, the insertion device can be removed from the application site and the application procedure is completed.

In a further variant not shown in the figures, but which can be understood therefrom and from this description, the infusion set is not secured on the housing in such a way as to be struck off it by the hammer head, and instead the infusion set is attached to the hammer head itself. This means that the upper end of the infusion set is brought into connection with the lower end of the hammer head. This can be done, for example, by adhesive bonding, frictional engagement or a form-fit. In some cases, the infusion set can be plugged onto or into the hammer head. In this case, the hammer head can, for example, have an extension which engages into a corresponding recess in the infusion set, for example with an exact fit, to hold the infusion set by frictional engagement. Of course, this can also be reversed, that is to say the infusion set has an extension and the hammer head has a corresponding recess.

The infusion set can also engage round the hammer head with a clamping action so as to be secured thereon, or vice versa. Care is taken to ensure that, during the movement in the drive direction, neither the infusion set nor the hammer head comes into contact with the housing, so as to avoid unnecessary friction losses upon conversion of the potential energy of the drive means into the kinetic energy of the infusion set. This allows the infusion device to be made compact, without excessively large drive means.

Figure 9:
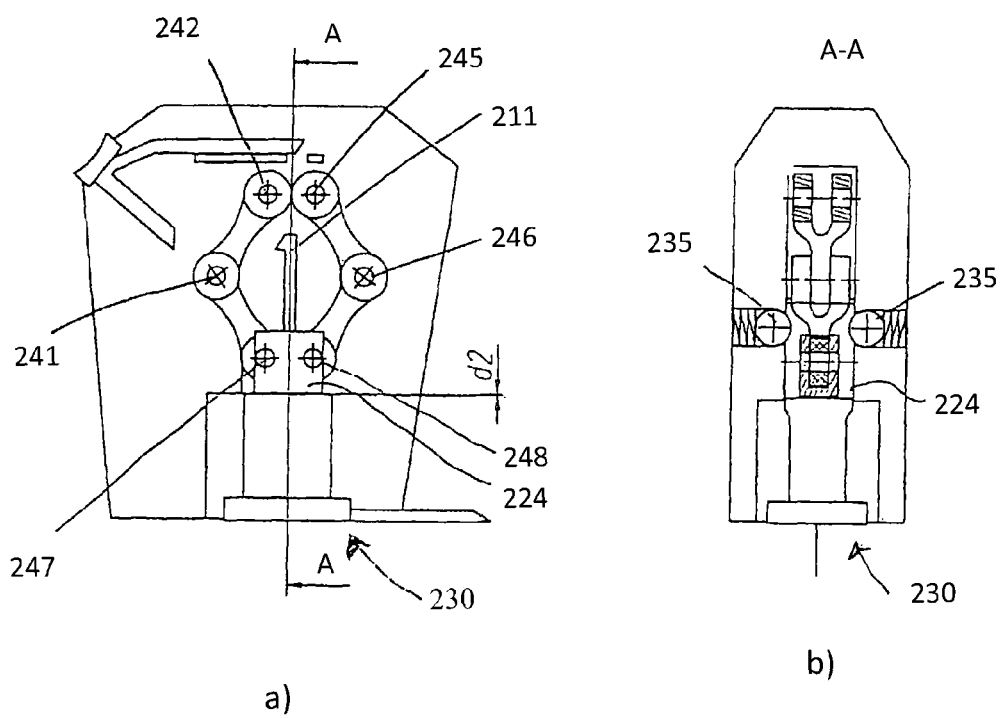
FIG. 9, including
Figure 13A:
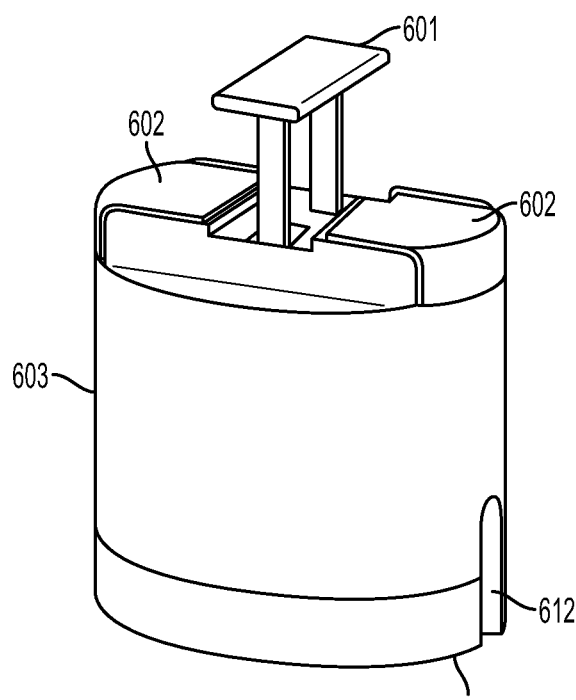
FIGS. 13a and 13b, shows another embodiment of the present invention.
Figure 13B:
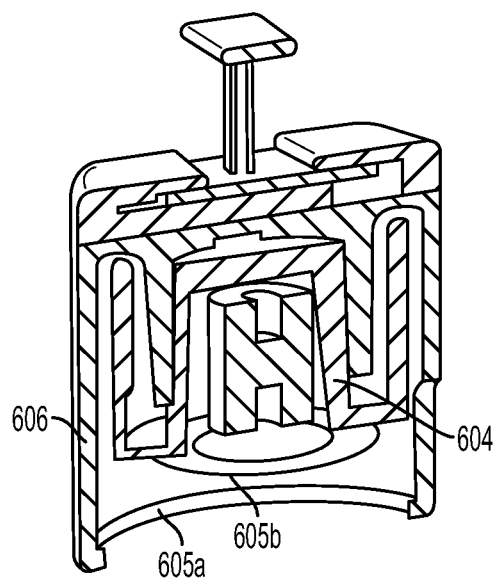

FIG. 9 also illustrates the principle of the present invention, with identical reference numbers designating the same parts as in the embodiment described above. The variant of the second embodiment described with reference to FIGS. 8 and 9 is similar to this. Referring to FIG. 9, a lateral introduction of the infusion set into the inserter or insertion device is described. The insertion set 230 is pushed laterally in the direction E1 into the insertion device. The distance between the hammer head 224 and the upper end 238 of the infusion set is designated by "d1". This distance can be 0 or greater than 0 as in the previous embodiment. A guide 250 serves as abutment surface for the infusion set in order to orient the latter correctly with respect to the hammer 224. Correspondingly, in the second embodiment, the rear wall 236 shown in FIG. 4 can be designed to guide the infusion set when it is introduced into the insertion device. The lateral introduction of the infusion set can also be provided in the other embodiments. For example, in the sixth embodiment (FIGS. 13 to 16), a gap 612 at the side (FIG. 13a) is provided for this purpose.

Figure 10A:
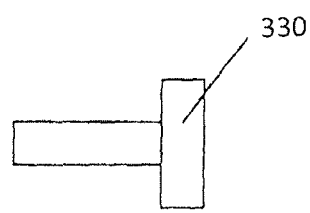
FIGS. 10a, 10b and 10c, shows another embodiment of the present invention.
Figure 10B:
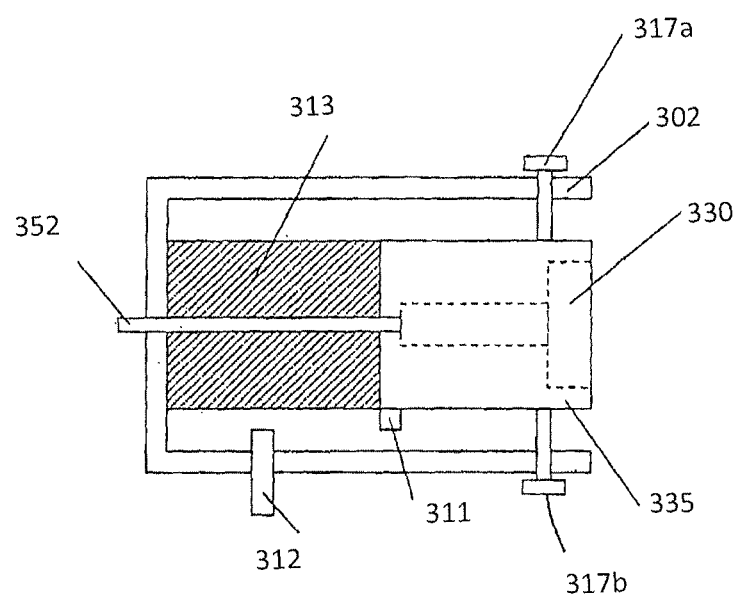
Figure 10C:
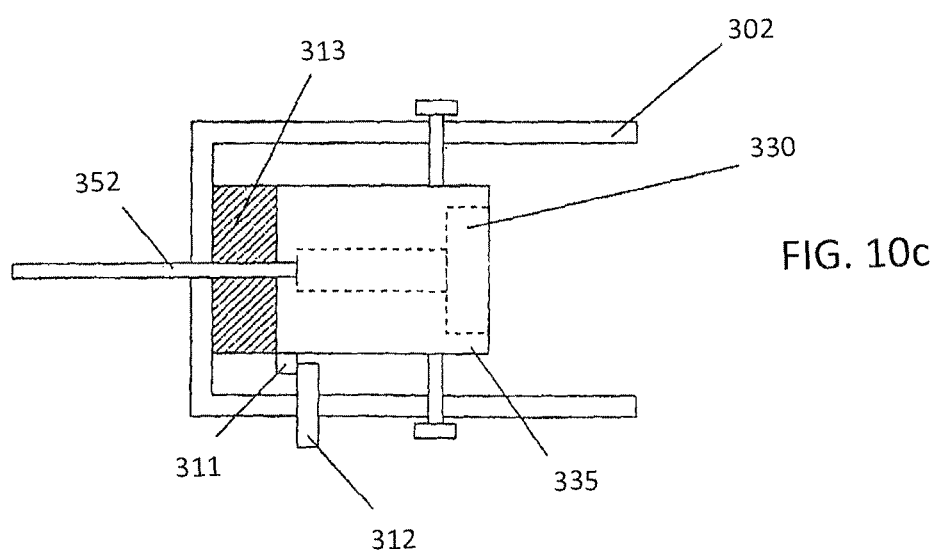

FIG. 10 shows a further embodiment of the present invention, in which an elastic means serves both as a guide for the drive endpiece and also as a drive mechanism. In the embodiment shown in FIG. 10, the elastic means is formed from an elastic material and assumes an elongate shape, with constant cross section in the longitudinal direction, so that, in the released state, its distance from the housing is constant along the entire longitudinal extent. The elastic means may be formed from any suitable elastic material, for example, a foam, rubber, etc. FIG. 10a shows the infusion set which, in FIG. 10b, is inserted into the receiving element 335. The receiving element serves to hold the infusion set, for example by frictional engagement or with a force fit. The grips 317a and 317b extend in a longitudinal slit of the housing and are used for charging the insertion device, by the elastic means 313 being brought from a released state (FIG. 10b) to a tensioned state (FIG. 10c). In this process, the cam 311 engages in the release button 312. The ejector 352 is entrained in this movement. If the release button 312 is now moved away from the cam 311 in FIG. 10c, the energy stored in the elastic means 313 discharges and drives the drive endpiece 335, at the same time designed as receiving element, in the drive direction. After the infusion set has thus been applied to the skin, the ejector 352 serves to release the infusion set from the receiving element 335.

Figure 11:
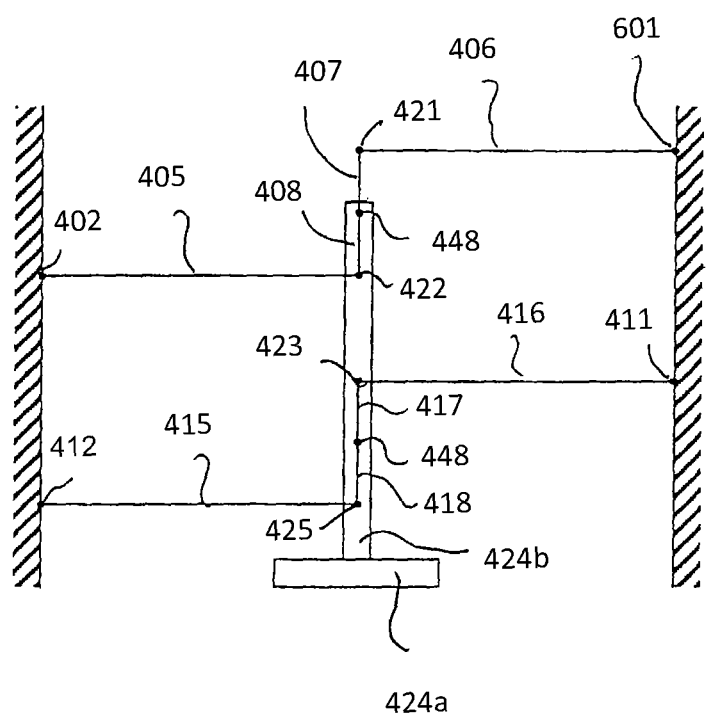
FIG. 11 shows another embodiment of the present invention.

FIG. 11 shows another embodiment of the present invention in which a drive endpiece is designed in the form of a punch or an inverted T. The drive endpiece has a lower end 424a onto which an infusion set can be fitted, or which is designed to strike the latter out of a holding fixture which, for example, is secured on a housing wall. The drive endpiece also has a part 424b which extends in the drive direction and which is here referred to as connecting rod. Pivot bearings 448 and 447 are mounted on this connecting rod and each serve as rotary connection members for levers 408, 407 and 417, 418, respectively. The rotary connection members 421, 422, 423 and 425 are not fixedly connected to the connecting rod 424, but only via the levers 407, 408, 417 and 418. These rotary connection members are in turn connected in each case via leg levers 405, 406, 415 and 416 to rotary connection members or pivot bearings 401, 402, 411, 412 on the housing wall. The embodiment shown permits guidance of the connection endpiece along a lemniscate curve and may, therefore, also be referred to as a lemniscate guide. The connecting rod is guided at least substantially vertically by this. The elastic tensioning means and the locking mechanism and release mechanism can be designed analogously to the other described embodiments. The elastic means can be connected to the connecting rod and/or to one or more of the leg levers so as to pretension these in such a way that the connection endpiece is accelerated downward when the tension of the elastic means is released.

FIG. 12 shows a further embodiment of the invention. A leg lever 505 is attached at one end on the housing wall 502 via a rotary connection member 542. An infusion set 530 is secured at the opposite end of the leg lever. The leg lever can be tensioned against the housing wall 502 via a spring 513 as is shown in FIG. 12b. If a locking mechanism (not shown) is released, the leg lever 505 is forced downward by the spring 513, as is shown in FIG. 12a. If a free end of the leg lever strikes against an abutment 503, the infusion set 530 can be released, for example from a frictional connection, and, after a short free flight, can penetrate the skin.

Instead of the abutment, it is of course also possible to provide an ejector mechanism with which the infusion set can be released from the insertion device after it has penetrated the skin. Alternatively, the infusion set can also be struck out of a holding fixture by the leg lever 505, as has been described in other embodiments.

FIGS. 13 to 16 show another embodiment of the present invention. FIG. 13a shows the insertion device in the tensioned state, that is to say the charging grip 601 is drawn upward. The release mechanism 602 is located to the left and right of the charging grip. These are pressed inward for release. The housing is designated by 603 and surrounds a drive endpiece 604, which can be seen in FIG. 13b. An elastomer part 605 is located at the lower end of the housing 603 and may be suitably connected, including integrally connected, to the latter. This elastomer part 605 is guided round a sleeve 606 at the lower end of the insertion device, as can be seen from FIG. 13b. The elastomer part bears on the lower inside wall of the sleeve 606 at a location designated by 605a. From there, it branches upward in the form of a band 605b. FIG. 13b also shows the tensioned state.

Figure 14C:
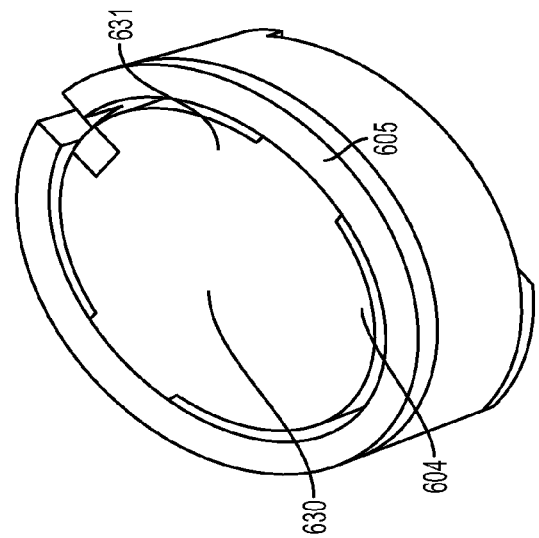
FIGS. 14a to 14c, shows further views of the embodiment of FIG. 13.
Figure 14B:
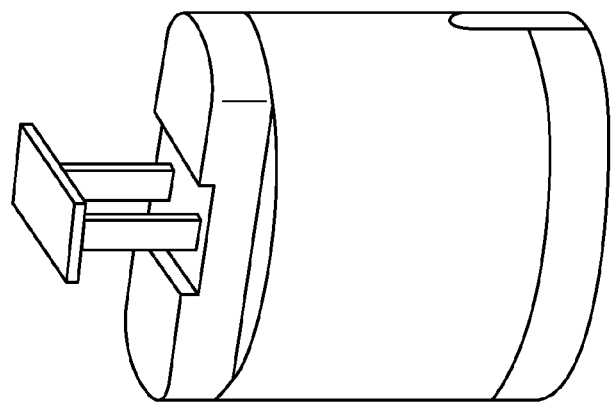
Figure 14A:
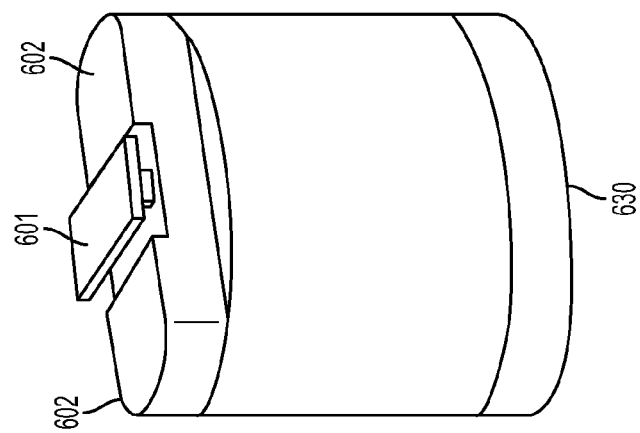

FIG. 14 shows the non-tensioned state in which the charging grip 601 has moved downward after the release mechanisms 602 have been actuated. A needle tip 630 can be seen at the bottom protruding downward from the insertion device. FIG. 14b corresponds to FIG. 13a. FIG. 14c shows the state of FIG. 14a with the infusion needle 630 and the liner or plaster 631. The drive endpiece 604 is located at the lower end of its path of movement. The lowermost end of the drive endpiece 604 lies at least approximately in the plane of the lower end of the elastomer part 605. As can be seen from FIG. 14c, there is a space between the lower end 605 of the elastomer part and the drive endpiece 604.

Figure 15C:
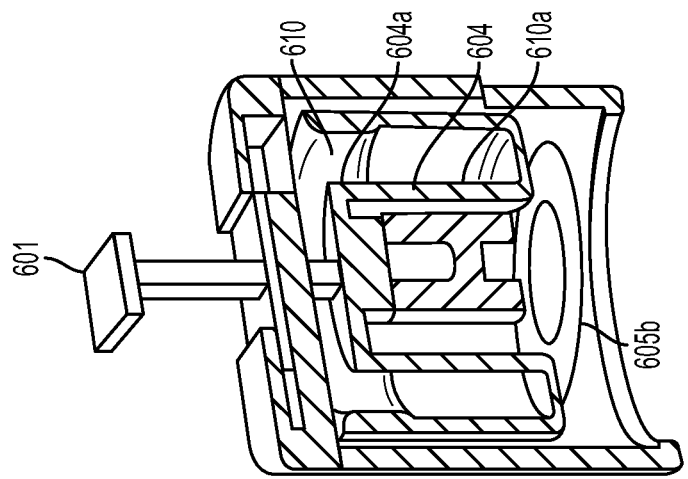
FIGS. 15a to 15c, shows further views of the embodiment of FIG. 13.
Figure 15B:
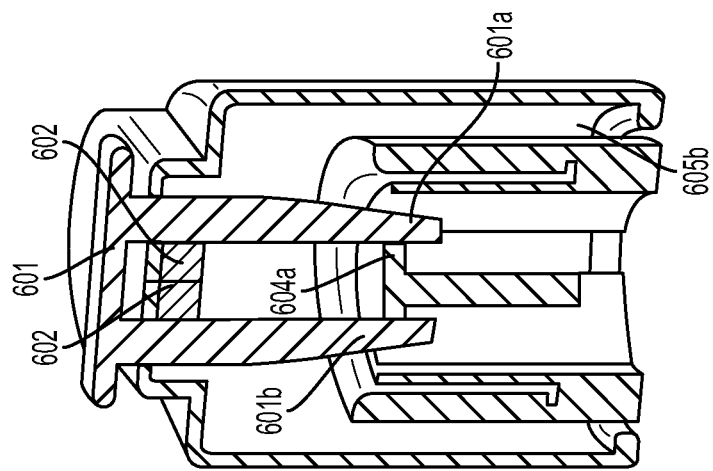
Figure 15A:
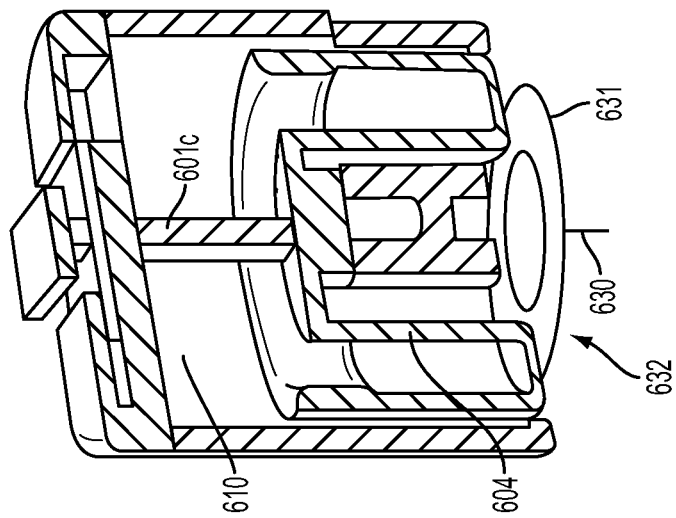

FIG. 15a shows, in cross section, the non-tensioned state from FIG. 14a. The infusion set 632 is mounted in the drive endpiece 604. Hooks 610 are engaged with the drive endpiece 604 and define the deepest position of the path of movement of the drive endpiece.

As will be seen from FIG. 15b, the band 605b of the elastomer part is guided round a top end of the drive endpiece, such that the band is stretched when the drive endpiece is moved upward. The upward movement is effected with the aid of the charging grip 601. At its lower end, this charging grip has two hooks 601a and 601b which are locked in engagement with a correspondingly designed projection 604a of the drive endpiece. This locked engagement can be released by the release mechanisms 602 because, when the charging grip 601 is drawn out, they act on extensions 601c which can be seen in FIG. 15a.

FIG. 15c shows the tensioned state in cross section. The band 605b is tensioned, and the insertion device is ready for application, the drive endpiece 604 being moved downward until extensions 604a strike against the hook-shaped ends 610a.

Figure 16:
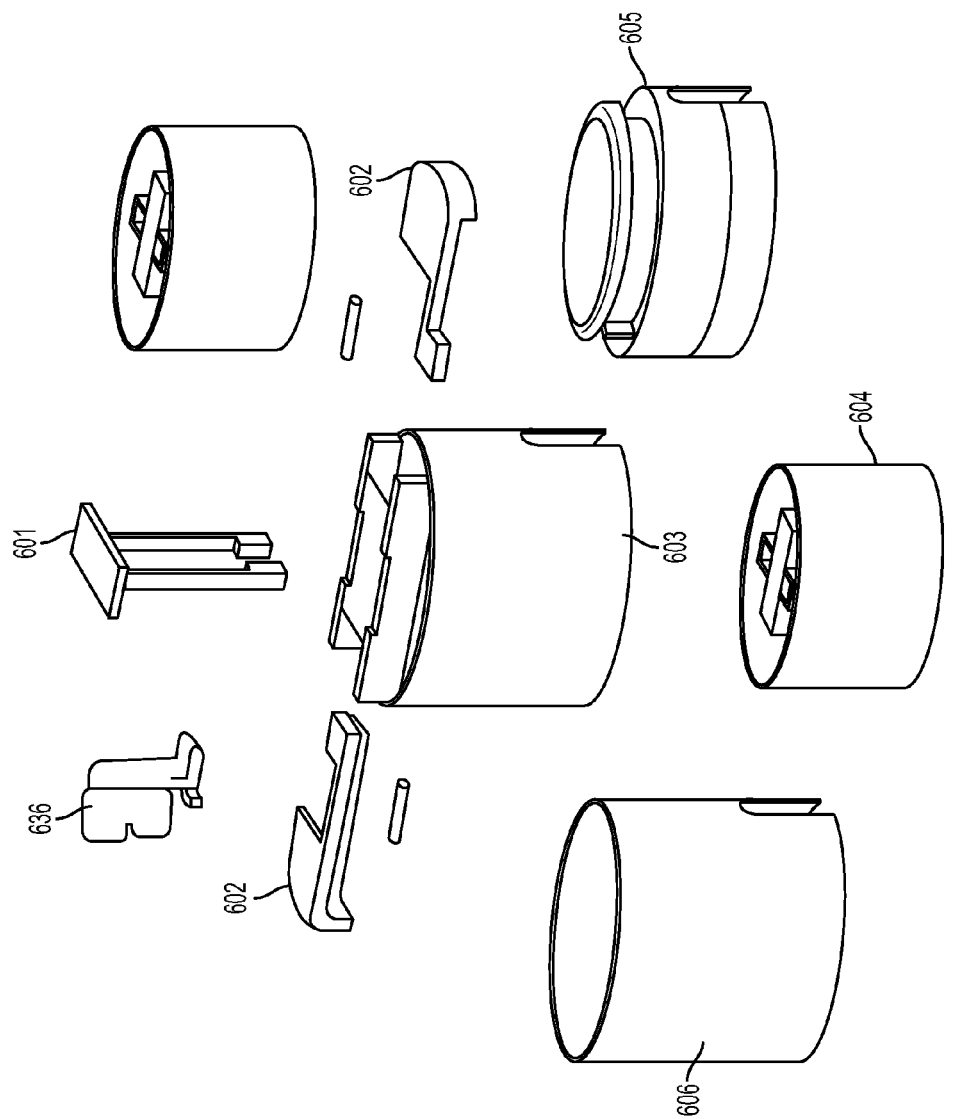
FIG. 16 shows component parts of the embodiment of FIG. 13.

FIG. 16 shows component parts of the insertion device of FIGS. 13 to 15. Here, 606 indicates the sleeve, 601 the charging grip, 602 the release mechanisms, 636 a guard for the needle, 604 the drive endpiece, 605 the elastomer part, and 603 the housing.

Embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principles of the invention and the practical application thereof, and to enable one of ordinary skill in the art to utilize the invention in various embodiments and with various modifications as are suited to the use contemplated. All such modifications and variations are within the scope of the invention as determined by the appended claims when interpreted in accordance with the breadth they are fairly, legally, and equitably entitled.

The invention claimed is:

1. An insertion device for infusion sets, said insertion device comprising:
   a housing for enclosing an infusion set;
   a drive device comprising a drive endpiece for displacing the infusion set for insertion;
   at least one rotary connection member on a side wall of the housing;
   at least one leg lever connected at a first end to the at least one rotary connection member;
   an elastic member for pretensioning the at least one leg lever against the side wall, a second end of the at least one leg lever remote from the first end for receiving the infusion set or striking the infusion set out of a holding fixture, the at least one leg lever pivoted via at least one rotary connection member when the tension of the elastic member is removed by a release mechanism; and
   an infusion set holder configured to hold the infusion set within the insertion device such that the infusion set is entirely spaced-apart from the housing, and such that prior to actuation of the insertion device, the infusion set is arranged proximate the drive endpiece and configured to enable the drive endpiece to pass the infusion set holder without contacting the holder and, upon actuation of the insertion device, the drive endpiece carries the infusion set to release the infusion set from the holder.

2. The insertion device as claimed in claim 1, wherein the at least one leg lever comprises portions that move in the insertion direction and is configured such that said portions are either spaced apart from the housing or do not execute any sliding movement relative to the housing.

3. The insertion device as claimed in claim 1, at least some of the rotary connection members are movable in the insertion direction.

4. The insertion device as claimed in claim 3, wherein at least two first oppositely turning rotary connection members are movable in the insertion direction, and their drive movement is synchronized by the coupled rotational movement of two second positionally fixed rotary connection members, one of the first rotary connection members in each case being connected to one of the second rotary connection members via the at least one leg lever.

5. The insertion device as claimed in claim 1, wherein the at least one leg lever is articulated on the housing at least laterally from the insertion direction to guide the drive endpiece in the insertion direction.

6. The insertion device as claimed in claim 5, wherein the at least one leg lever comprises a lemniscate guide which guides a drive member in the insertion direction.

7. The insertion device as claimed in claim 5, wherein the at least one leg lever is articulated on the housing in at least one position and the drive endpiece rotates about said position via at least one leg lever without making contact with the housing.

8. An insertion device for piercing devices such as infusion sets, said device comprising:
   a housing for enclosing a piercing device to be placed in the insertion device;
   at least one rotary connection member on a side wall of the housing;
   at least one leg lever connected at a first end to the at least one rotary connection member;
   an elastic member for pretensioning the at least one leg lever against the side wall, a second end of the at least one leg lever remote from the first end for receiving an infusion set or striking an infusion set out of a holding fixture, the at least one leg lever pivoted via at least one rotary connection member when the tension of the elastic member is removed by a release mechanism;
   a drive device for moving the piercing device in an insertion direction; and
   a piercing device holder configured to hold the piercing device prior to actuation of the insertion device such that the piercing device is entirely spaced-apart from the housing, wherein the piercing device holder is configured to enable a portion of the drive device to pass the piercing device holder upon actuation of the insertion device without contacting the holder and, upon actuation of the insertion device, the drive device movement in the insertion direction carries the piercing device to release the piercing device from the holder.

9. The insertion device as claimed in claim 8, wherein a drive endpiece is moved in the insertion direction when the pretensioning is released.

10. The insertion device as claimed in claim 8, the elastic member elastically expanded when the drive endpiece is moved counter to the insertion direction.

11. The insertion device as claimed in claim 10, wherein the elastic member comprises several expandable bands arranged substantially symmetrically around a drive endpiece to maintain the drive endpiece on an intended path of movement in the insertion direction, the drive endpiece remaining at a distance from the housing on the path of movement.

12. The insertion device as claimed in claim 11, wherein the drive endpiece is designed for application of an infusion set.

13. The insertion device as claimed in claim 12, wherein the piercing device holder comprises an infusion set holder for application of an infusion set, the holder configured such that the drive endpiece, when moved in the insertion direction, strikes an applied infusion set out of the holder, and the drive device is designed such that, in the pretensioned state, there is no contact between applied infusion set and drive endpiece.

14. An insertion device for infusion sets, said insertion device comprising:
  a housing for enclosing an infusion set;
  a drive device comprising a drive endpiece for displacing the infusion set for insertion; and
  an infusion set holder comprising at least two receiving elements within the insertion device configured to hold the infusion set between the at least two receiving elements such that, prior to actuation of the insertion device, the infusion set is entirely spaced-apart from the housing, and the infusion set is arranged proximate the drive endpiece and configured to enable the drive endpiece to pass between the at least two receiving elements without contacting the at least two receiving elements and, upon actuation of the insertion device, the drive endpiece carries the infusion set to release the infusion set from the at least two receiving elements; and
  wherein at least two first oppositely turning rotary connection members are movable in the insertion direction, and their drive movement is synchronized by the coupled rotational movement of two second positionally fixed rotary connection members, one of the first rotary connection members in each case being connected to one of the second rotary connection members via a leg lever.

15. An insertion device for infusion sets, said insertion device comprising:
  a housing for enclosing an infusion set;
  a drive device comprising a drive endpiece for displacing the infusion set for insertion; and
  an infusion set holder configured to hold the infusion set within the insertion device prior to actuation; and
  wherein at least two first oppositely turning rotary connection members are movable in the insertion direction, and their drive movement is synchronized by the coupled rotational movement of two second positionally fixed rotary connection members, one of the first rotary connection members in each case being connected to one of the second rotary connection members via a leg lever.

16. The insertion device as claimed in claim 15, wherein the housing comprises elongate slits, and wherein the drive endpiece extends through the elongate slits.

* * * * *